US007543149B2

United States Patent
Ricciardi et al.

(10) Patent No.: US 7,543,149 B2
(45) Date of Patent: Jun. 2, 2009

(54) METHOD, SYSTEM AND COMPUTER PRODUCT FOR SECURING PATIENT IDENTITY

(75) Inventors: Thomas N. Ricciardi, Portland, OR (US); Curtis White, Sherwood, OR (US)

(73) Assignee: GE Medical Systems Information Technologies Inc., Milwaukee, WI (US)

( * ) Notice: Subject to any disclaimer, the term of this patent is extended or adjusted under 35 U.S.C. 154(b) by 603 days.

(21) Appl. No.: 10/420,218

(22) Filed: Apr. 22, 2003

(65) Prior Publication Data

US 2004/0215981 A1 Oct. 28, 2004

(51) Int. Cl.
*H04L 9/00* (2006.01)

(52) U.S. Cl. .................. 713/176; 713/180; 713/181; 707/6; 705/51

(58) Field of Classification Search .......... 713/176, 713/181, 180; 705/2–3
See application file for complete search history.

(56) References Cited

U.S. PATENT DOCUMENTS

| | | | | |
|---|---|---|---|---|
| 5,689,799 | A | 11/1997 | Dougherty et al. | 455/2 |
| 5,876,926 | A | 3/1999 | Beecham | 435/5 |
| 6,061,789 | A | 5/2000 | Hauser et al. | 713/168 |
| 6,363,525 | B1 | 3/2002 | Dougherty et al. | 725/34 |
| 6,397,224 | B1* | 5/2002 | Zubeldia et al. | 707/102 |
| 2001/0054155 | A1* | 12/2001 | Hagan et al. | 713/193 |
| 2002/0010679 | A1* | 1/2002 | Felsher | 705/51 |
| 2002/0116227 | A1* | 8/2002 | Dick | 705/3 |
| 2004/0172293 | A1* | 9/2004 | Bruschi et al. | 705/2 |
| 2005/0165623 | A1* | 7/2005 | Landi et al. | 705/2 |

OTHER PUBLICATIONS

HIPAA. "Researcher Solves Privacy Problem". HIPAA Archive. Apr. 4, 2003. www.healthdatamanagement.com/html/hipaa/NewsStory.cfm?DID=9951.
"About FieldEncrypt". ResearchSafe, Inc. 2003. www.devguru.com/Products/FieldEncrypt/index.html.

* cited by examiner

*Primary Examiner*—Nasser G Moazzami
*Assistant Examiner*—Fikremariam Yalew
(74) *Attorney, Agent, or Firm*—Hanley, Flight & Zimmerman, LLC; Peter Vogel; Michael Della Penna

(57) ABSTRACT

A method for securing patient identity comprising accessing an electronic medical records database including patient data for a plurality of patients. Each patient in the electronic medical records database is assigned a unique patient identifier. Patient data for a first patient, including a first patient identifier, is retrieved from the electronic medical records database. The first patient is de-identified from the patient data. De-identifying includes the creation of a first encoded patient identifier responsive to the first patient identifier. The de-identifying results in de-identified first patient data and includes the replacement of the first patient identifier with the first encoded patient identifier. The de-identified first patient data is transmitted to a data warehouse system. The method further comprises identifying a second patient in response to receiving report data that includes a second encoded patient identifier from the data warehouse system. The identifying includes the creation of a second patient identifier responsive to the second encoded patient identifier.

18 Claims, 3 Drawing Sheets

METHOD, SYSTEM AND COMPUTER PRODUCT FOR SECURING PATIENT IDENTITY

BACKGROUND OF INVENTION

The present disclosure relates generally to a method for securing patient identity and in particular, to a method for de-identifying patient data at an ambulatory patient care provider (PCP) site for submission to a data warehouse system and then re-identifying a patient, at the PCP site, from de-identified patient data received from the data warehouse system.

Data warehousing methods have been used to aggregate, clean, stage, report and analyze patient information derived from medical claims billing and electronic medical records (EMR). Patient data may be extracted from multiple EMR databases located at PCP sites in geographically dispersed locations, then transported and stored in a centrally located data warehouse. The central data warehouse may be a source of information for population-based profile reports of physician productivity, preventative care, disease-management statistics and research on clinical outcomes. Patient data is sensitive and confidential, and therefore, specific identifying information must be removed prior to transporting it from a PCP site to a central data warehouse. This removal of identifying information must be performed per the federal Health Insurance Portability and Accountability Act (HIPAA) regulations. Any data that is contained in a public database must not reveal the identity of the individual patients whose medical information is contained in the database. Because of this requirement, any information contained on a medical report or record that could aid in tracing back to a particular individual must be removed from the report or record prior to adding the data to a data warehouse for public data mining.

In order to accurately assess the impact of a particular drug or treatment on a patient it is helpful to analyze all medical reports relating to the particular patient. Removing data that can be used to trace back to an individual patient can make it impossible to group and analyze all medical reports relating to a particular patient. In addition, one of the aims of population analysis is to assemble an at-risk cohort population comprised of individuals who may be candidates for clinical intervention. However, de-identified data is not very useful to the patient care providers who need to know the identity of their own patients in order to treat them.

SUMMARY OF INVENTION

One aspect of the invention is a method for securing patient identity. The method comprises accessing an electronic medical records database including patient data for a plurality of patients. Each patient in the electronic medical records database is assigned a unique patient identifier. Patient data for a first patient, including a first patient identifier, is retrieved from the electronic medical records database. The first patient is de-identified from the patient data. De-identifying includes the creation of a first encoded patient identifier responsive to the first patient identifier. The de-identifying results in de-identified first patient data and includes the replacement of the first patient identifier with the first encoded patient identifier. The de-identified first patient data is transmitted to a data warehouse system. The method further comprises identifying a second patient in response to receiving report data that includes a second encoded patient identifier from the data warehouse system. The identifying includes the creation of a second patient identifier responsive to the second encoded patient identifier.

Another aspect of the invention is a method for securing patient identity. The method comprises accessing an electronic medical records database including patient data for a plurality of patients. Each patient in the electronic medical records database is assigned a unique patient identifier. Patient data for a first patient, including a first patient identifier, is retrieved from the electronic medical records database. The first patient is de-identified from the patient data, resulting in de-identified first patient data. The de-identifying includes the creation of a first encoded patient identifier responsive to the first patient identifier. The creation of a first encoded patient identifier includes: receiving a user entered password string; hashing the user entered password string into a sixteen digit number; and summing the sixteen digit number with said first patient identifier, resulting in the first encoded patient identifier. The de-identifying further includes replacing the first patient identifier with the first encoded patient identifier, and removing or transforming identifying data from the patient data for a first patient that may be used to identify the first patient. The de-identified first patient data is transmitted to a data warehouse system. The method further comprises identifying a second patient in response to receiving report data that includes a second encoded patient identifier from the data warehouse system. The identifying includes the creation of a second patient identifier by subtracting the sixteen digit number from the second encoded patient identifier, resulting in a second patient identifier.

Another aspect of the invention is a system for securing patient identity. The system comprises a network, a storage device, and a patient care provider system in communication with the storage device and the network. The patient care provider system includes software to implement a method. The method comprises accessing an electronic medical records database including patient data for a plurality of patients. Each patient in the electronic medical records database is assigned a unique patient identifier. Patient data for a first patient, including a first patient identifier, is retrieved from the electronic medical records database. The first patient is de-identified from the patient data. De-identifying includes the creation of a first encoded patient identifier responsive to the first patient identifier. The de-identifying results in de-identified first patient data and includes the replacement of the first patient identifier with the first encoded patient identifier. The de-identified first patient data is transmitted to a data warehouse system. The method further comprises identifying a second patient in response to receiving report data that includes a second encoded patient identifier from the data warehouse system. The identifying includes the creation of a second patient identifier responsive to the second encoded patient identifier.

A further aspect of the invention is a computer program product for securing patient identity. The computer program product comprises a storage medium readable by a processing circuit and storing instructions for execution by the processing circuit for implementing a method. The method comprises accessing an electronic medical records database including patient data for a plurality of patients. Each patient in the electronic medical records database is assigned a unique patient identifier. Patient data for a first patient, including a first patient identifier, is retrieved from the electronic medical records database. The first patient is de-identified from the patient data. De-identifying includes the creation of a first encoded patient identifier responsive to the first patient identifier. The de-identifying results in de-identified first patient data and includes the replacement of the first patient identifier with the first encoded patient identifier. The de-identified first patient data is transmitted to a data warehouse system. The method further comprises identifying a second patient in response to receiving report data that includes a second encoded patient identifier from the data warehouse system. The identifying includes the creation of a second patient identifier responsive to the second encoded patient identifier.

A further aspect of the invention is a computer program product for securing patient identity. The computer program product comprises a storage medium readable by a processing circuit and storing instructions for execution by the processing circuit for implementing a method. The method comprises accessing an electronic medical records database including patient data for a plurality of patients. Each patient in the electronic medical records database is assigned a unique patient identifier. Patient data for a first patient, Including a first patient identifier, is retrieved from the electronic medical records database. The first patient is de-identified from the patient data, resulting in de-identified first patient data. The de-identifying includes the creation of a first encoded patient identifier responsive to the first patient identifier. The creation of a first encoded patient identifier includes: receiving a user entered password string; hashing the user entered password string into a sixteen digit number; and summing the sixteen digit number with said first patient identifier, resulting in the first encoded patient identifier. The de-identifying further includes replacing the first patient identifier with the first encoded patient identifier, and removing or transforming identifying data from the patient data for a first patient that may be used to identify the first patient. The de-identified first patient data is transmitted to a data warehouse system. The method further comprises identifying a second patient in response to receiving report data that includes a second encoded patient identifier from the data warehouse system. The identifying includes the creation of a second patient identifier by subtracting the sixteen digit number from the second encoded patient identifier, resulting in a second patient identifier. Further aspects of the invention are disclosed herein.

BRIEF DESCRIPTION OF DRAWINGS

Referring to the exemplary drawings wherein like elements are numbered alike in the several Figures.

DETAILED DESCRIPTION

An exemplary embodiment of the present invention is a secure process for sending de-identified patient information from an ambulatory patient care provider (PCP) site to a data warehouse system where the patient data may be analyzed and compared with a wider range of patient data. The terms "de-identified patient information" and "de-identified patient data" as used in this document refer to both fully de-identified data as defined by HIPAA and limited data set data as defined by HIPAA. A limited data set is protected health information for research, public health and health care operations that excludes direct identifiers (e.g., name; postal address other than city, state and zip code; social security number; medical records numbers) but in which other identifying information may remain (e.g., dates of examination; documentation; diagnosis; prescription; lab test results). This is contrasted with fully de-identified data as defined by HIPAA, where all data that may be used to trace back to an individual patient is removed from the record. Information obtained through the data warehouse that pertains to individual patients is transmitted back to the originating PCP site, via a cohort report. Cohort reports are generated by queries that are executed against the data warehouse system to identify patient cohort groups. The individual patients included in a cohort report are then re-identified at the PCP site so that the PCPs may consider the information when deciding on treatment options for the individual patients.

Figure 1:
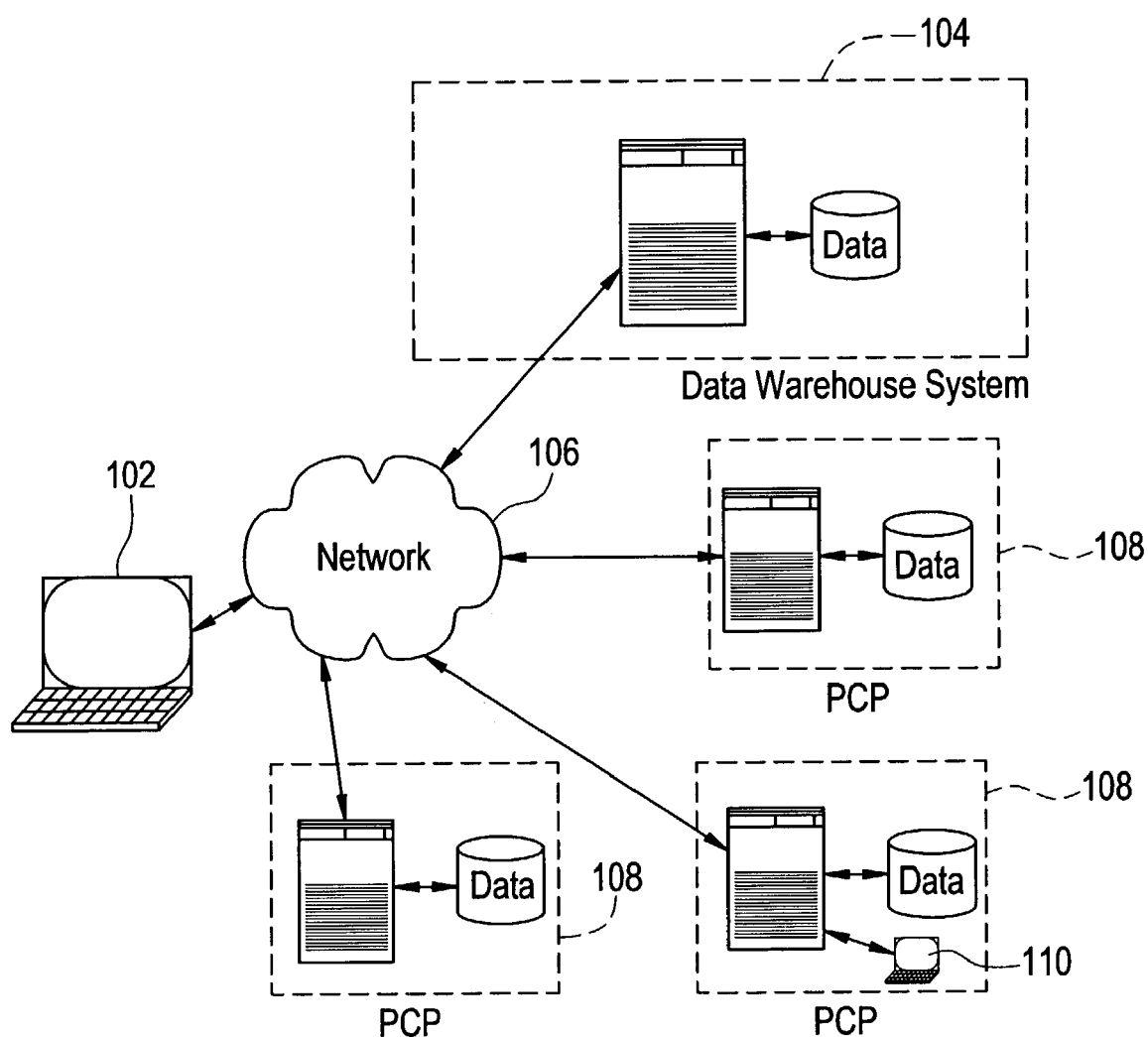
FIG. 1 is an exemplary system for securing patient identity.

FIG. 1 is an exemplary system for securing patient identity. PCP systems 108 located at various PCP sites are connected to a network 106. The PCP systems 108 send patient medical data to a data warehouse located on a data warehouse system 104. The PCP systems 108 typically include application software to perform data extraction along with one or more storage device for storing the electronic medical records (EMRs) associated with patients treated at the PCP site. In addition, the PCP systems 108 may include PCP user systems 110 to access the EMR data, to initiate the data extraction and to enter a password string to be used for encrypting a patient identifier. The PCP user systems 110 may be directly attached to the PCP system 108 or they may access the PCP system 108 via the network 106. Each PCP user system 110 may be implemented using a general-purpose computer executing a computer program for carrying out the processes described herein. The PCP user systems 110 may be personal computers or host attached terminals. If the PCP user systems 110 are personal computers, the processing described herein may be shared by a PCP user system 110 and a PCP system 108 by providing an applet to the PCP user system 110. The storage device located at the PCP system 108 may be implemented using a variety of devices for storing electronic information such as a file transfer protocol (FTP) server. It is understood that the storage device may be implemented using memory contained in the PCP system 108 or it may be a separate physical device. The storage device contains a variety of information including an EMR database.

In addition, the system of FIG. 1 includes one or more data warehouse user systems 102 through which an end-user may make a request to an application program on the data warehouse system 104 to access particular records stored in the data warehouse (e.g., to create a cohort report). In an exemplary embodiment of the present invention, end-users may include PCP staff members, pharmaceutical company research team members and personnel from companies that make medical products. The data warehouse user systems 102 may be directly connected to the data warehouse system 104 or they may be coupled to the data warehouse system 104 via the network 106. Each data warehouse user system 102 may be implemented using a general-purpose computer executing a computer program for carrying out the processes described herein. The data warehouse user systems 102 may be personal computers or host attached terminals. If the data warehouse user systems 102 are personal computers, the processing described herein may be shared by a data warehouse user system 102 and the data warehouse system 104 by providing an applet to the data warehouse user system 102.

The network 106 may be any type of known network including a local area network (LAN), a wide area network (WAN), an intranet, or a global network (e.g., Internet). A data warehouse user system 102 may be coupled to the data warehouse system 104 through multiple networks (e.g., intranet and Internet) so that not all data warehouse user systems 102 are required to be coupled to the data warehouse system 104 through the same network. Similarly, a PCP system 108 may be coupled to the data mining host system 104 through multiple networks (e.g., intranet and Internet) so that not all PCP systems 108 are required to be coupled to the data warehouse system 104 through the same network. One or more of the data warehouse user systems 102, the PCP systems 108 and the data warehouse system 104 may be connected to the network 106 in a wireless fashion and the network 106 may be a wireless network. In an exemplary embodiment, the network 106 is the Internet and each data warehouse user system 102 executes a user interface application to directly connect to the data warehouse system 104. In another embodiment, a data warehouse user system 102 may execute a web browser to contact the data warehouse system 104 through the network 106. Alternatively, a data warehouse user system 102 may be implemented using a device programmed primarily for accessing the network 106 such as WebTV.

The data warehouse system 104 may be implemented using a server operating in response to a computer program stored in a storage medium accessible by the server. The data warehouse system 104 may operate as a network server (often referred to as a web server) to communicate with the data warehouse user systems 102 and the PCP systems 108. The data warehouse system 104 handles sending and receiving information to and from data warehouse user systems 102 and PCP systems 108 and can perform associated tasks. The data warehouse system 104 may also include a firewall to prevent unauthorized access to the data warehouse system 104 and enforce any limitations on authorized access. For instance, an administrator may have access to the entire system and have authority to modify portions of the system and a PCP staff member may only have access to view a subset of the data warehouse records for particular patients. In an exemplary embodiment, the administrator has the ability to add new users, delete users and edit user privileges. The firewall may be implemented using conventional hardware and/or software as is known in the art.

The data warehouse system 104 also operates as an application server. The data warehouse system 104 executes one or more application programs to provide access to the data repository located on the data warehouse system, as well as application programs to import patient data into a staging area and then into the data warehouse. In addition, the data warehouse system 104 may also execute one or more applications to create patient cohort reports and to send the patient cohort reports to the PCP systems 108. Processing may be shared by the data warehouse user system 102 and the data warehouse system 104 by providing an application (e.g., java applet) to the data warehouse user system 102. Alternatively, the data warehouse user system 102 can include a stand-alone software application for performing a portion of the processing described herein. Similarly, processing may be shared by the PCP system 102 and the data warehouse system 104 by providing an application to the PCP system 102 and alternatively, the PCP system 102 can include a stand-alone software application for performing a portion of the processing described herein. It is understood that separate servers may be used to implement the network server functions and the application server functions. Alternatively, the network server, firewall and the application server can be implemented by a single server executing computer programs to perform the requisite functions.

The storage device located at the data warehouse system 104 may be implemented using a variety of devices for storing electronic information such as a file transfer protocol (FTP) server. It is understood that the storage device may be implemented using memory contained in the data warehouse system 104 or it may be a separate physical device. The storage device contains a variety of information including a data warehouse containing patient medical data from one or more PCPs. The data warehouse system 104 may also operate as a database server and coordinate access to application data including data stored on the storage device. The data warehouse may be physically stored as a single database with access restricted based on user characteristics or it can be physically stored in a variety of databases including portions of the database on the data warehouse user systems 102 or the data warehouse system 104. In an exemplary embodiment, the data repository is implemented using a relational database system and the database system provides different views of the data to different end-users based on end-user characteristics.

Figure 2:
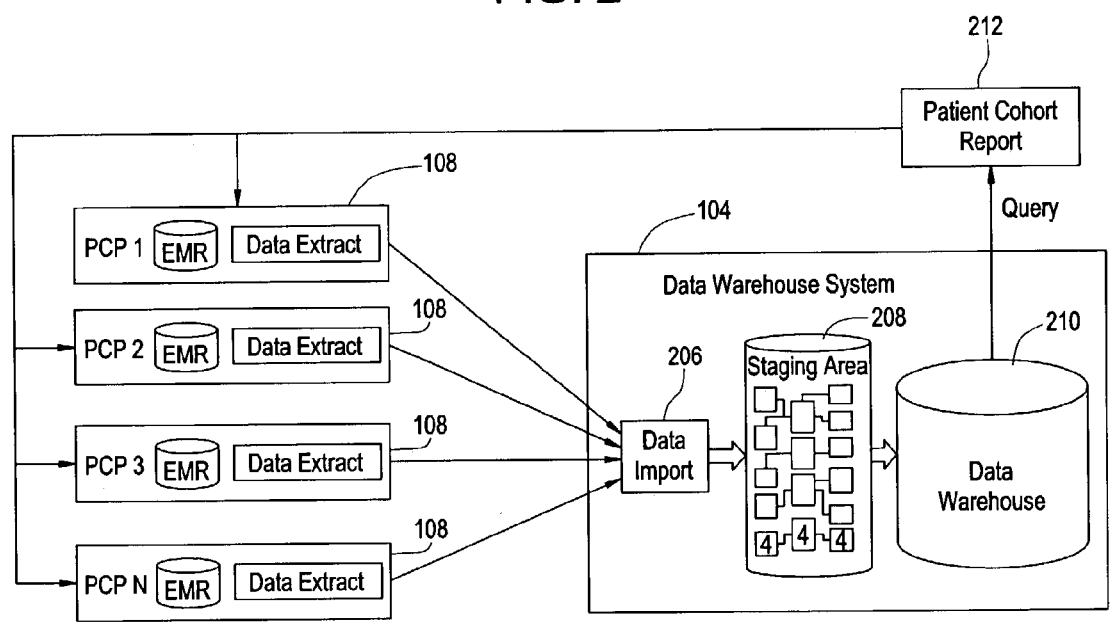
FIG. 2 is a block diagram of an exemplary data warehouse system architecture.

FIG. 2 is a block diagram of an exemplary data warehouse architecture. Patient data is extracted from EMR databases located in the PCP systems 108. In an exemplary embodiment of the present invention, an EMR database record includes data such as: patient name and address, medications, allergies, observations, diagnoses, and health insurance information. The PCP systems 108 include application software for extracting patient data from the EMR database. The data is then de-identified and transported (e.g., via Hypertext Transfer Protocol (HTTPS)) over the network 106 to the data warehouse system 104. The data warehouse system 104 includes application software to perform a data import function 206. The data import function 206 aggregates and cleanses de-identified patient data from multiple sites and then stores the data into a staging area 208. Data received from multiple PCP systems 108 is normalized, checked for validity and completeness, and either corrected or flagged as defective. Data from multiple PCP systems 108 is then combined together into a relational database. Aggregation, cleaning and staging data in the described fashion allows the data to be queried meaningfully and efficiently, either as a single entity or specific to each individual PCP site 108. The de-identified patient data is then staged into a data warehouse 210 where it is available for querying.

Patient cohort reports 212 are generated by application software located on the data warehouse system 104 and returned to the PCP systems 108 for use by the primary care providers in treating individual patients. Patient cohort reports 212 may be automatically generated by executing a canned query on a periodic basis. PCP staff members, pharmaceutical company research team members and personnel from companies that make medical products may each run patient cohort reports 212. In addition, patient cohort reports 212 may be created by an end-user accessing a data warehouse user system 102 to create custom reports or to initiate the running of canned reports. Further, patient cohort reports 212 may be automatically generated in response to the application software, located on the data warehouse system 104, determining that particular combinations of data for a patient are stored in the data warehouse. An exemplary patient cohort report 212 includes all patients with a particular disease that were treated with a particular medication. Another exemplary patient cohort report 212 includes patients of a particular age and sex who have particular test results. For example, a patient cohort report 212 may list all women with heart disease who are taking a hormone replacement therapy drug. The patient cohort report 212 would list all the patients with records in the data warehouse 210 that fit this criteria along with a warning about the possible side-effects and the likelihood of the side-effects occurring. In an exemplary embodiment, each PCP site receives the entire report, in another embodiment, each PCP site receives the report only for patients that are being treated at the PCP site.

Figure 3:
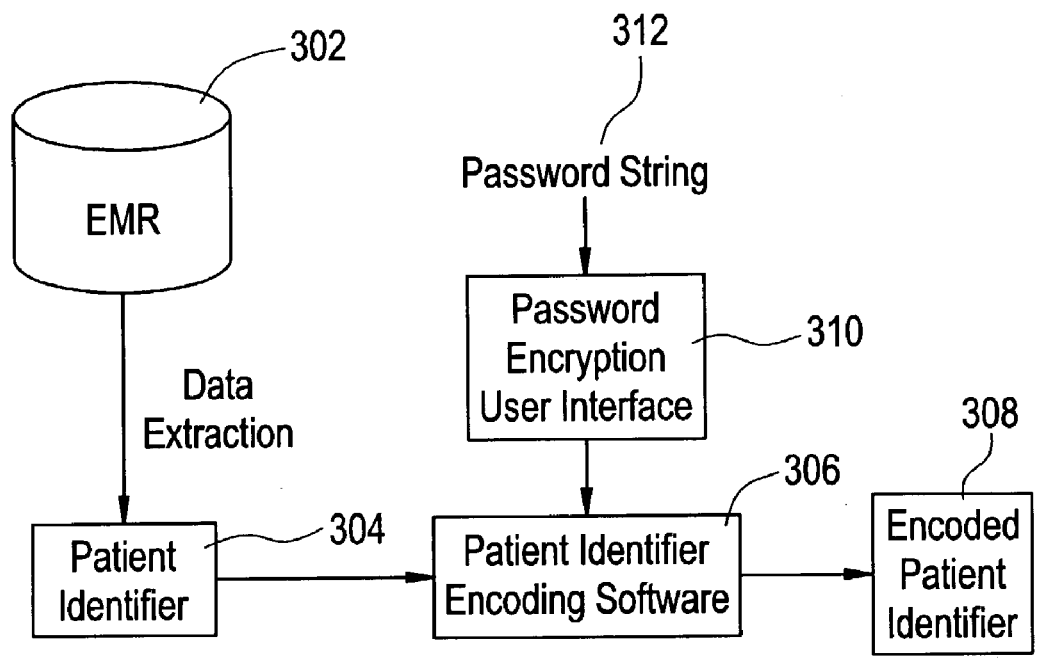
FIG. 3 is a block diagram of an exemplary process for de-identifying patient data during data extraction.
Figure 4:
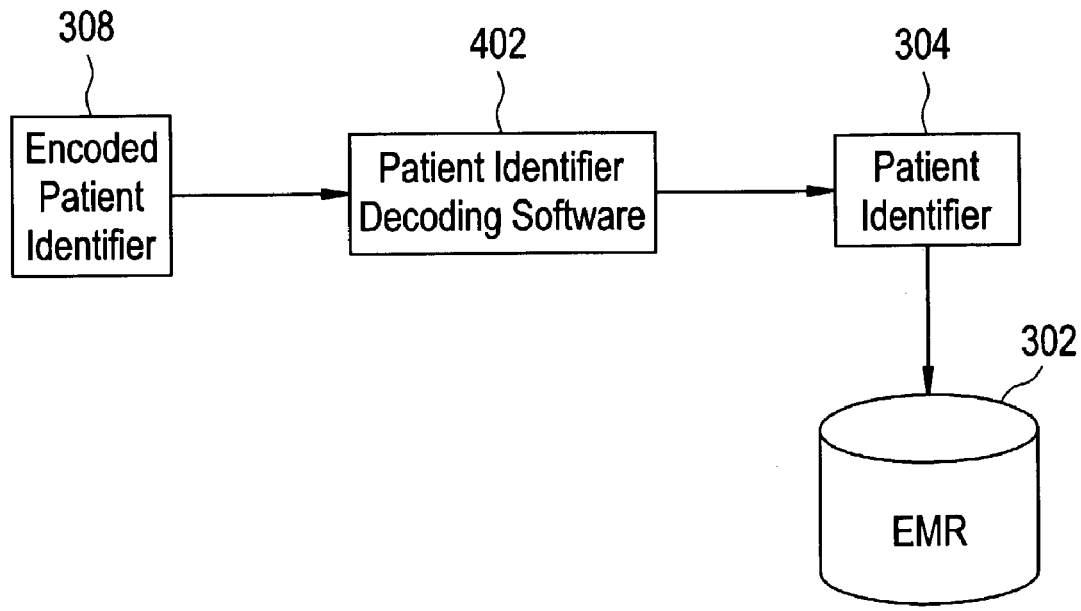
FIG. 4 is a block diagram of an exemplary process for re-identifying a patient from de-identified patient data.

In an exemplary embodiment of the present invention, the ability to create patient cohort reports 212 based on querying longitudinal patient data is supported by the ability to connect all records relating to a single patient in the data warehouse 210. This requires a unique identifier to be associated with each patient record that is transmitted to the data warehouse 210. The unique identifier must not be traceable back to an individual patient by end-users accessing the data warehouse 210. However, individual PCPs may want to retain the ability to re-identify a patient based on the unique identifier so that the medical personnel located at the PCP site can follow through with the patient in response to information included in the patient cohort reports 212. FIG. 3 depicts an exemplary process for de-identifying patient data for storage in a data warehouse 210 located at the data warehouse system 104 and FIG. 4 depicts an exemplary process for re-identifying a patient from the de-identified patient data contained in a patient cohort report 212.

FIG. 3 is a block diagram of an exemplary process for de-identifying patient data during data extraction for transmission to a data warehouse system 104. The de-identification process removes information that will identify a patient while still retaining clinically useful information about the patient. Patient data is extracted from the EMR database 302 and identifying information is removed, resulting in de-identified patient data. In an exemplary embodiment of the present invention, an EMR database 302 includes the following patient identifying demographic data: names; geographic identifiers, including address; dates directly related to an individual, including birth date, admission date, discharge date and date of death; telephone and fax numbers; electronic mail addresses; social security number; medical record number; health plan beneficiary; account numbers; certificate or license numbers; vehicle identifiers and serial numbers including license plate numbers; device identifiers and serial numbers, web Universal Resource Locators (URLs) and internet protocol (IP) address numbers; biometric identifiers, including finger and voice prints; full face photographic images and comparable images; other unique identifying numbers, characteristics and codes assigned by the PCP or by the EMR system for administrative purposes, including a patient identifier (PID) 304. The EMR database 302 also includes information about: the patient diagnosis or problem; medications taken or prescribed; observations, diagnostic laboratory tests and vital signs; subjective and objective findings, assessments, orders, plans, and notes documented by healthcare providers. The EMR database 302 also includes audit information that records the date, time, and identity of persons who have created, read, updated, or deleted information from the patient record. The EMR database 302 record for each patient also contains a numeric key known as the PID 304 which may be used to uniquely identify an individual patient. The PID 304 is encoded as part of the de-identification process to create an encoded patient identifier (EPID) 308. The EPID 308 is sent, along with the de-identified patient data, to the data warehouse system 104.

The extraction process is performed by application software located on the PCP system 108 and may be executed in the background on a periodic basis (e.g., at 2 a.m. every night, at 2 a.m. every Saturday). In this manner, the extraction process will be less likely to interfere with existing software located on the PCP system 108. The extraction process may also be initiated by a remote system (e.g., the data warehouse system 104) and may include full or incremental back-up schemes. In an exemplary embodiment of the present invention, the following identifiers are removed or transformed in order to create de-identified data that would be classified under the HIPAA definition as fully de-identified data: name, geographic subdivisions smaller than a state including street address, city, county, precinct, zip code (down to the last three digits), dates directly related to an individual (e.g., birth date), phone and fax numbers, electronic mail addresses, health plan number, account number, certificate/license number, device identifier and serial numbers, unified resource locator (URL), internet protocol (IP) address, biometric identifiers, full face photograph, and other unique identifying numbers, characteristics or codes.

In an alternate exemplary embodiment of the present invention, the following identifiers are removed or transformed in order to create de-identified that that would be classified under the HIPAA definition as limited data set information: direct identifiers such as name, postal address (other than city, state and zip code), social security number and medical records numbers. In the limited data set information implementation of the present invention some identifying information may remain such as dates of examination, documentation, diagnosis, prescription and lab test results.

A novel EPID 308 is assigned to each patient based on the PID 304 associated with the patient and a password entered by the PCP. The PID 304 to EPID 308 mapping is not maintained persistently. As depicted in the exemplary embodiment shown in FIG. 3, a password string 312 is supplied by the PCP via a password encryption user interface 310 on the PCP user system 110. This password string 312 is known only to the PCP and is required in order to decode the EPID 308 into a PID 304. The user at the PCP site must have the password string 312 to obtain the PID 304 and this password string 312 must be re-entered each time a patient is to be re-identified. The password encryption user interface 310 may be a graphical user interface. In an exemplary embodiment of the present invention, the user entered password string 312 is encoded using the two-fish algorithm. The two-fish algorithm, as known in the art, is a secret-key block cipher cryptography algorithm that is designed to be highly secure and highly flexible. It utilizes a single key for both encryption and decryption and is often referred to as symmetric encryption. The encoding is performed by patient identifier encoding software 306 located on the PCP system 108. The patient identifier encoding software 306 also hashes the encoded password string to produce a sixteen-digit number. This sixteen-digit number is numerically added to the PID 304 to create the EPID 308. Other methods of creating the EPID 308 from the PID 304 may be utilized with an exemplary embodiment of the present invention (e.g Rivest, Shamir and Adelman, or RSA) as long as the EPID may only be decoded at the PCP site.

FIG. 4 is a block diagram of an exemplary process for re-identifying a patient from de-identified patient data. As described previously, population cohort reports 212 of at-risk patients are created by running queries against the data warehouse 210. De-identified individuals may be tracked longitudinally and queried as members of anonymous population cohorts, based on clinical selection criteria. The query result, contained in the cohort report 212, is a list of EPIDs 308. A list of patient EPIDs 308 in a patient cohort report 212 are received by the PCP system 108. The EPIDs 308 are read into the patient identifier decoding software 402, located on the PCP system 108, and the original PID 304 is recreated. The PID 304 may be used as a key to look up additional identifying information from the EMR database 302. Employees of the PCP may utilize the patient-specific information from the EMR database 302 to counsel the patient and to decide on treatment alternatives.

An embodiment of the present invention allows for ambulatory PCPs to send patient data into a data warehouse containing patient data from other ambulatory PCPs. In this manner, patient data may be analyzed and compared to a larger population of patients. The de-identified patient data includes an EPID 308 that may be useful in creating longitudinal reports that analyze more than one record for a particular patient. The effects of certain drugs and treatments on patient cohort groups can be analyzed and may lead to improvements in the use or composition of the drugs and treatments. In addition, an embodiment of the present invention allows for the PCP to receive cohort reports 212 based on data contained in the data warehouse. These patient cohort reports 212 include an EPID 308 for each patient. The EPID 308 may be decoded at the PCP site that created the EPID 308 and used to identify a particular patient. In this manner a PCP, by considering the information contained in the cohort report, may be able to provide improved treatment to the patient. This ability to provide useful information back to a patient level may also lead more PCPs to participate in sending patient data to a data warehouse. Having more data in the data warehouse may provide more useful information to third parties such as pharmaceutical companies, medical device companies and physicians about the effects and risks of particular treatments, while minimizing the risk of disclosing patient-identifying information to third parties. This may lead to improvements in preventative care as well as other types of medical care.

As described above, the embodiments of the invention may be embodied in the form of computer-implemented processes and apparatuses for practicing those processes. Embodiments of the invention may also be embodied in the form of computer program code containing instructions embodied in tangible media, such as floppy diskettes, CD-ROMs, hard drives, or any other computer-readable storage medium, wherein, when the computer program code is loaded into and executed by a computer, the computer becomes an apparatus for practicing the invention. An embodiment of the present invention can also be embodied in the form of computer program code, for example, whether stored in a storage medium, loaded into and/or executed by a computer, or transmitted over some transmission medium, such as over electrical wiring or cabling, through fiber optics, or via electromagnetic radiation, wherein, when the computer program code is loaded into and executed by a computer, the computer becomes an apparatus for practicing the invention. When implemented on a general-purpose microprocessor, the computer program code segments configure the microprocessor to create specific logic circuits.

While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Moreover, the use of the terms first, second, etc. do not denote any order or importance, but rather the terms first, second, etc. are used to distinguish one element from another.

The invention claimed is:

1. A method for securing patient identity, the method comprising:

accessing an electronic medical records database including patient data for a plurality of patients, wherein each said patient is assigned a unique patient identifier;

retrieving said patient data for a first patient from said electronic medical records database, wherein said patient data for said first patient includes a first patient identifier;

de-identifying said first patient from said patient data for said first patient including the creation of a first encoded patient identifier responsive to said first patient identifier, wherein said de-identifying results in de-identified first patient data and includes the replacement of said first patient identifier with said first encoded patient identifier;

transmitting said de-identified first patient data to a data warehouse system;

connecting data relating to said first patient in said data warehouse; and identifying a second patient in response to receiving report data including a second encoded patient identifier from said data warehouse system, wherein said identifying includes the creation of a second patient identifier responsive to said second encoded patient identifier, wherein said creation of said first encoded patient identifier includes:

receiving a user entered password string;

hashing said user entered password string into a sixteen digit number; and summing said sixteen digit number with said first patient identifier resulting in said first encoded patient identifier.

2. The method of claim 1 wherein said patient data includes a name, a geographic identifier, a birth date, an admission date, a telephone number, a social security number, a medical record number, an account number, and diagnosis data.

3. The method of claim 1 wherein said de-identifying further includes removing or transforming identifying data from said patient data for said first patient that may be used to identify said first patient.

4. The method of claim 3 wherein said identifying data includes name, geographic subdivisions smaller than state, phone number, health plan number, account number, unified resource locator, internet protocol address and biometric identifiers.

5. The method of claim 1 wherein said creation of said second patient identifier includes accessing an encryption key and applying said encryption key to said second encoded patient identifier.

6. The method of claim 1 wherein said de-identified first patient data includes fully de-identified data.

7. The method of claim 1 wherein said de-identified first patient data includes limited data set data.

8. The method of claim 1 wherein said report data is a patient cohort report.

9. The method of claim 8 wherein said patient cohort report is created by running a query against a data warehouse located on said data warehouse system.

10. The method of claim 1 wherein said data warehouse is a relational database and provides different views of the data to different users based on user characteristics.

11. The method of claim 1 wherein said data warehouse includes data for a plurality of patient care providers.

12. The method of claim 1 wherein said retrieving, de-identifying and transmitting are performed on a periodic basis.

13. The method of claim 1 wherein said retrieving, de-identifying and transmitting are initiated from said data warehouse system.

14. The method of claim 1 wherein said plurality of patients are ambulatory patients.

15. The method of claim 1 wherein said first patient and said second patient are the same patient, said first patient identifier and said second patient identifier contain the same value, and said first encoded patient identifier and said second encoded patient identifier contain the same value.

16. The method of claim 1 further comprising retrieving said patient data for said second patient from said electronic medical records database using said second patient identifier as a key into said electronic medical records database.

17. A method for securing patient identity, the method comprising:

accessing an electronic medical records database including patient data for a plurality of patients, wherein each said patient is assigned a unique patient identifier;

retrieving said patient data for a first patient from said electronic medical records database, wherein said patient data for said first patient includes a first patient identifier;

de-identifying said first patient from said patient data for said first patient resulting in de-identified first patient data, wherein said de-identifying includes:

creating a first encoded patient identifier responsive to said first patient identifier, wherein said creating includes:

receiving a user entered password string;

hashing said user entered password string into a sixteen digit number; and summing said sixteen digit number with said first patient identifier resulting in said first encoded patient identifier;

replacing said first patient identifier with said first encoded patient identifier; and removing or transforming identifying data from said patient data for said first patient that may be used to identify said first patient;

transmitting said de-identified first patient data to a data warehouse system; and identifying a second patient in response to receiving report data including a second encoded patient identifier from said data warehouse system, wherein said identifying includes subtracting said sixteen digit number from said second encoded patient identifier resulting in a second patient identifier.

18. A computer program product for securing patient identify, the product comprising:

a storage medium readable by a processing circuit and storing instructions for execution by the processing circuit for:

accessing an electronic medical records database including patient data for a plurality of patients, wherein each said patient is assigned a unique patient identifier;

retrieving said patient data for a first patient from said electronic medical records database, wherein said patient data for said first patient includes a first patient identifier;

de-identifying said first patient from said patient data for said first patient resulting in de-identified first patient data, wherein said de-identifying includes:

creating a first encoded patient identifier responsive to said first patient identifier, wherein said creating includes:

receiving a user entered password string;

hashing said user entered password string into a sixteen digit number; and summing said sixteen digit number with said first patient identifier resulting in said first encoded patient identifier;

replacing said first patient identifier with said first encoded patient identifier; and removing or transforming identifying data from said patient data for said first patient that may be used to identify said first patient;

transmitting said de-identified first patient data to a data warehouse system; and identifying a second patient in response to receiving report data including a second encoded patient identifier from said data warehouse system, wherein said identifying includes subtracting said sixteen digit number from said second encoded patient identifier resulting in a second patient identifier.

* * * * *